United States Patent
Mian et al.

(10) Patent No.: US 7,602,937 B2
(45) Date of Patent: Oct. 13, 2009

(54) IMAGE-BASED VISIBILITY MEASUREMENT

(75) Inventors: Zahid F. Mian, Loudonville, NY (US); William G. vonAchen, Latham, NY (US)

(73) Assignee: International Electronic Machines Corporation, Albany, NY (US)

( * ) Notice: Subject to any disclaimer, the term of this patent is extended or adjusted under 35 U.S.C. 154(b) by 748 days.

(21) Appl. No.: 11/149,089

(22) Filed: Jun. 8, 2005

(65) Prior Publication Data

US 2005/0270537 A1 Dec. 8, 2005

Related U.S. Application Data

(60) Provisional application No. 60/577,590, filed on Jun. 8, 2004.

(51) Int. Cl.
*G06K 9/00* (2006.01)
(52) U.S. Cl. .................................. 382/100; 382/286
(58) Field of Classification Search ............... 346/4.07, 346/456, 482; 382/106, 199, 100, 286; 356/432, 356/433, 434, 436, 437; 340/601; 702/3; 73/170.16, 170.27
See application file for complete search history.

(56) References Cited

U.S. PATENT DOCUMENTS 5,434,778 A 7/1995 Nylander
5,880,836 A 3/1999 Lonnqvist
6,085,152 A * 7/2000 Doerfel ........................ 702/3
2003/0197867 A1 * 10/2003 Kwon .......................... 356/437
2004/0101200 A1 * 5/2004 Peele et al. ................. 382/218

OTHER PUBLICATIONS

Kwon, T., "An Automatic Visibility Measurement System Based on Video Cameras," University of Minnesota, Department of Electrical and Computer Engineering, Apr. 2000.

* cited by examiner

*Primary Examiner*—Andrew W Johns
(74) *Attorney, Agent, or Firm*—John W. LaBatt; Hoffman Warnick LLC

(57) ABSTRACT

The invention provides an image-based visibility measurement solution in which an image is used to calculate a visibility (visual range). In one embodiment, a lighting condition for the image is determined and the visibility calculation is adjusted based on the lighting condition. Further, the invention can obtain image data for a set of portions of the image and estimate a visual range based on each portion. The estimated visual ranges can be combined to calculate the visibility for the image. Still further, multiple metrics can be calculated, each of which is used to estimate a visual range. Subsequently, the visual ranges can be used to calculate the visibility for the image. Even further, configuration data that is based on a set of training images can be used to calculate the visibility for a new image. To this extent, the invention can incorporate the lighting condition, portions of the image having differing features, multiple metrics, and/or feedback through training images to accurately measure visibility based on an image.

30 Claims, 13 Drawing Sheets

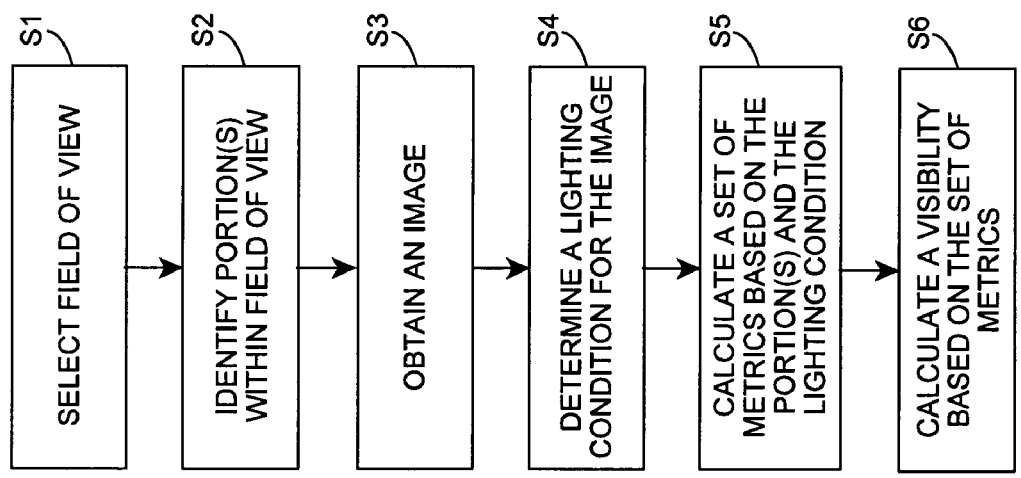

IMAGE-BASED VISIBILITY MEASUREMENT

REFERENCE TO RELATED APPLICATION

The current application claims the benefit of co-pending U.S. Provisional Application No. 60/577,590, filed on Jun. 8, 2004, which is hereby incorporated herein by reference.

GOVERNMENT LICENSE RIGHTS

The U.S. Government has a paid-up license in this invention and the right in limited circumstances to require the patent owner to license others on reasonable terms as provided for by the terms of Contract Number DG133R-03-CN-0069 awarded by the National Oceanic and Atmospheric Administration of the U.S. Department of Commerce.

BACKGROUND OF THE INVENTION

1. Technical Field

The invention relates generally to measuring visibility, and more particularly, to an image-based solution for measuring visibility.

2. Background Art

Visibility, or visual range, is the distance at which a target object of a given size and characteristics can be seen. Knowledge of visibility is important for transportation, meteorological, and environmental applications. For example, visibility can be used to monitor safety conditions and/or impose a speed limit along a waterway, highway, or the like. Similarly, visibility is important in take off and landing aircraft, monitoring weather conditions like fog and precipitation, and monitoring haze and air pollution in industrial areas and wildlife reserves.

In general, the visibility of a target object is dependent on its "contrast". Contrast is defined as the ratio of the difference of the luminance of the target object and its background to the luminance of the background. A target object having a contrast that exceeds a particular threshold, generally 0.02, is considered visible. To this extent, the visual range can be defined as the distance from a target object at which the contrast of the target object drops to 0.02.

With respect to visibility, the "extinction coefficient", or attenuation coefficient, is a measure of an amount of visibility loss over a given distance. Extinction is caused by two major factors. The first is light scattering, which is the deflection of light from one path into another, and is caused, for example, by some atmospheric components. Light scattering contributes to extinction by scattering light from a target object out of the line of vision, thereby reducing the total incoming light from the target, and by scattering light from other directions into the line of vision, thereby adding spurious light signatures to those received from the target. The second primary cause of extinction is light absorption, which reduces the light available to arrive from the target object, and is caused, for example, by other components of the atmosphere.

Historically, a lack of visibility, e.g., due to heavy rain, fog, snow, or the like, has contributed to more accidents in the various travel modalities, and particularly air travel, than virtually any other cause. As a result, a number of solutions have been proposed to evaluate and/or monitor visibility conditions. For example, a transmissometer measures fluctuations in light received from a known source. Alternatively, a nephelometer measures light scattering based on the light scattered by an aerosol. Additionally, a scattered light meter estimates the total amount of scattered light that is received, and a teleradiometer, or light meter, measures the total brightness of a particular target object.

However, each of these solutions is limited. For example, the transmissometer requires widely separated, precisely aligned components, and fails to account for extra light that is scattered into the field of view. The nephelometer and scattered light meter do not measure the loss of light due to absorption, and the teleradiometer is limited to measuring the amount of light that arrives from the bearing of the target and is sensitive to non-uniform lighting and variations in inherent contrast.

In order to compensate for one or more non-measured components in these solutions, model-based calculations and/or a combination of multiple solutions into a single package have been proposed. However, even alone, these solutions are expensive, often large, and the results provided do not always accord with visual estimates provided by trained observers. In particular, most commercial visibility sensors determine scattering properties within a relatively small air volume and use a transfer algorithm to convert the observation into a distance measurement. However, the measurements are based on the clarity of the air, and not the distance at which an individual can see a target object. To this extent, the same air quality may correspond to a wide range of visibilities based on the target object, lighting condition, and the like.

Other visibility measurement solutions propose the use of a video-based measurement approach. Such an approach offers a number of potential advantages, such as similarity to what is seen by a human, highly quantitative image data, as well as the availability of large image databases that can be used to prototype a solution from a set of known standardized materials. However, current video-based solutions are limited by requiring specialized and standardized target objects for measurement, require expensive, fragile equipment, provide variable results based on the time of day, lighting, and other factors, and require power consumption that makes deployment outside of an urban or suburban area questionable, if not impossible.

Scattering is characterized by the scattering coefficient, S, while absorption is characterized by the absorption coefficient, A. To this extent, the extinction coefficient, $\alpha$, is given by:

$$\alpha = S + A.$$

Additionally, an inherent contrast, $C_0$, of the target object is the contrast of the target object at a zero distance. Based on the Koschmieder relationship, at a distance, r, the corresponding contrast, $C_r$, can be calculated by:

$$C_r = C_0 e^{-\alpha r}.$$

This equation makes several assumptions: (1) that the extinction coefficient does not vary in the horizontal direction, i.e., that the atmosphere is homogenous; (2) that the background is the sky; and (3) that the sky radiance is the same at the target object as it is at the observer.

Using a black target object (e.g., $C_0 = -1$), visibility, V, can be determined as the distance, r, at which $C_r$ reduces to 0.02. This yields the equation:

$$V = \frac{\ln(1/0.02)}{\alpha} = \frac{3.912}{\alpha}$$

A transmissometer and/or nephelometer can be used to measure the extinction coefficient, a, and the equation above can be used to derive the visibility. Alternatively, the extinction coefficient can be determined by placing two black target objects at different distances, $r_1$ and $r_2$, from an observation point. Using a telephotometer, the contrasts, $C_1$ and $C_2$, for the respective black target objects from the observation point can be determined. Subsequently, the extinction coefficient can be calculated by:

$$\alpha = \left| \frac{\ln C_1 - \ln C_2}{r_1 - r_2} \right|$$

By directly or indirectly assuming that the decay of contrast follows the Koschmeider equation, existing solutions have several weaknesses. In particular, the Koschmeider equation assumes that the background is the sky and that the extinction coefficient remains constant along the path of vision. Neither of these assumptions is valid. For example, in determining the visibility of an aircraft pilot, clouds may be present and/or the pilot may be looking downward towards a prospective landing spot, the background of which is the ground. Further, the visual range may vary from region to region. As a result, a single measurement of the extinction coefficient will fail to account for these differences. For example, a fogbank may obscure a freeway for a short distance, while the rest of the field of view remains clear. Still further, the contrast of a target object, in terms of luminance, may vary significantly due to variations in sunlight, shadows, cloud cover, etc., while an observer's perception of the visibility of the target object remains substantially the same. Still further, a human will take into account other factors, such as the sharpness of features, clarity of texture, distinctiveness of color, and the like, when determining the target object's visibility.

To this extent, a need exists for an improved image-based visibility measurement solution that is not limited by one or more of these weaknesses.

SUMMARY OF THE INVENTION

The invention provides an image-based visibility measurement solution in which an image is used to calculate a visibility (visual range). In one embodiment, a lighting condition for the image is determined and the visibility calculation is adjusted based on the lighting condition. Further, the invention can obtain image data for a set (one or more) of portions of the image and estimate a visual range based on each portion. The estimated visual ranges can be combined to calculate the visibility for the image. Still further, multiple metrics can be calculated, each of which is used to estimate a visual range. Subsequently, the visual ranges can be used to calculate the visibility for the image. Even further, configuration data that is based on a set of training images can be used to calculate the visibility for a new image. To this extent, the invention can incorporate the lighting condition, portions of an image having differing features, multiple metrics, and/or feedback through training images to accurately measure visibility based on an image.

A first aspect of the invention provides a system for measuring visibility, the system comprising: means for obtaining an image; means for determining a lighting condition for the image; means for calculating a visibility based on the image; and means for adjusting the means for calculating based on the lighting condition.

A second aspect of the invention provides a system for measuring visibility, the system comprising: means for obtaining an image; means for obtaining image data for a set of portions of the image; means for estimating a set of visual ranges, wherein each estimated visual range is based on the image data for one of the set of portions; and means for calculating the visibility based on the set of visual ranges.

A third aspect of the invention provides a system for measuring visibility, the system comprising: means for obtaining an image; means for calculating a plurality of metrics based on the image; means for estimating a plurality of visual ranges, wherein each of the plurality of visual ranges is based on one of the plurality of metrics; and means for calculating the visibility based on the plurality of visual ranges.

A fourth aspect of the invention provides a system for measuring visibility, the system comprising: means for obtaining configuration data, wherein the configuration data is based on a set of training images; means for obtaining a new image; and means for calculating the visibility based on the configuration data and the new image.

A fifth aspect of the invention provides a method for measuring visibility, comprising: obtaining an image; determining a lighting condition for the image; calculating a visibility based on the image; and adjusting the calculating step based on the lighting condition.

A sixth aspect of the invention provides a method for measuring visibility, comprising: obtaining an image; obtaining image data for a set of portions of the image; estimating a set of visual ranges, wherein each estimated visual range is based on the image data for one of the set of portions; and calculating the visibility based on the set of visual ranges.

A seventh aspect of the invention provides a method for measuring visibility, comprising: obtaining an image; calculating a plurality of metrics based on the image; estimating a plurality of visual ranges, wherein each of the plurality of visual ranges is based on one of the plurality of metrics; and calculating the visibility based on the plurality of visual ranges.

An eighth aspect of the invention provides a method for measuring visibility, comprising: obtaining configuration data, wherein the configuration data is based on a set of training images; obtaining a new image; and calculating the visibility based on the configuration data and the new image.

A ninth aspect of the invention provides a computer-readable medium that includes computer program code to enable a computer infrastructure to measure visibility, the computer-readable medium comprising computer program code for performing the method steps of the invention.

A tenth aspect of the invention provides a business method for measuring visibility, the business method comprising managing a computer infrastructure that performs each of the steps of the invention; and receiving payment based on the managing step.

An eleventh aspect of the invention provides a method of generating a system for measuring visibility, the method comprising: obtaining a computer infrastructure; and deploying means for performing each of the steps of the invention to the computer infrastructure.

The illustrative aspects of the present invention are designed to solve the problems herein described and other problems not discussed, which are discoverable by a skilled artisan.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which:

FIG. 3 shows illustrative method steps that can be performed according to one embodiment of the invention;

It is noted that the drawings of the invention are not to scale. The drawings are intended to depict only typical aspects of the invention, and therefore should not be considered as limiting the scope of the invention. In the drawings, like numbering represents like elements between the drawings.

DETAILED DESCRIPTION

As indicated above, the invention provides an image-based visibility measurement solution in which an image is used to calculate a visibility (visual range). In one embodiment, a lighting condition for the image is determined and the visibility calculation is adjusted based on the lighting condition. Further, the invention can obtain image data for a set (one or more) of portions of the image and estimate a visual range based on each portion. The estimated visual ranges can be combined to calculate the visibility for the image. Still further, multiple metrics can be calculated, each of which is used to estimate a visual range. Subsequently, the visual ranges can be used to calculate the visibility for the image. Even further, configuration data that is based on a set of training images can be used to calculate the visibility for a new image. To this extent, the invention can incorporate the lighting condition, portions of the image having differing features, multiple metrics, and/or feedback through training images to accurately measure visibility based on an image.

Figure 1:
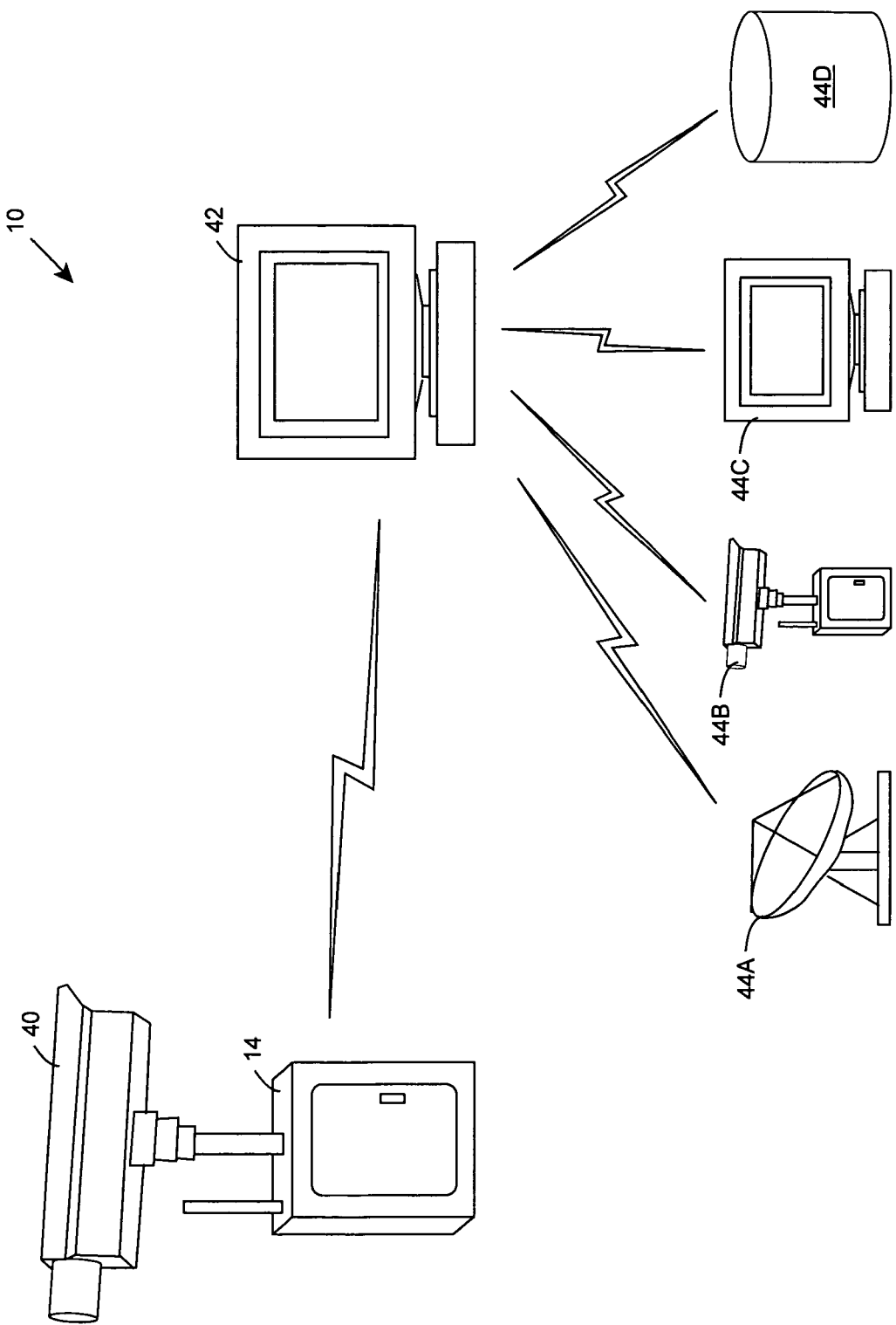
FIG. 1 shows an illustrative environment for measuring visibility.

Turning to the drawings, FIG. 1 shows an illustrative environment 10 for measuring visibility. In particular, environment 10 includes an image capture system 40 in communication with a computing device 14. In operation, image capture system 40 captures and provides an image to computing device 14, which performs the various process steps described herein to measure visibility. The imaging sensor for image capture system 40 can be selected based on one or more requirements for a particular application, such as a visibility sensor range, a target object size, a target object distance, a range of contrasts on a target object, and the like. Similarly, the optical components for image capture system 40 can be selected based on one or more requirements such as the modulation transfer function (MTF), resolution (e.g., line pairs), a spectral range, etc. Further, the imaging system for image capture system 40 can be selected based on a sensitivity (e.g., a lux level), a sensor size, a spectral response, an image sensing technology, progressive scan versus frame transfer, electronic shuttering, a fixed or adjustable focus, etc. In one embodiment, image capture system 40 comprises a standard digital video camera and/or digital still camera. Alternatively, image capture system 40 could comprise a standard analog video/still camera. In the latter case, an analog-to-digital converter can be included to transform the analog data into a digital signal that can be processed by computing device 14.

Further, image capture system 40 may be permanently pointed in one direction, may be able to scan across multiple fields of view, may have a motorized zoom, and/or may be a panoramic or wide field design imaging device. In one embodiment, image capture system 40 includes a small, motorized pan-tilt mechanism that enables image capture system 40 to cover a large field of view by scanning up to a 360 degree scene. Such a mechanism can repeatedly provide fully encoded and highly accurate positioning. Alternatively, image capture system 40 could comprise a small image scanner that can scan parts of the scene and focus them one part at a time, use an innovative optics/scanning arrangement in a small form-factor, and/or use panoramic imaging devices (e.g., mirrors or lenses) that enable the capture of image data in a 360 degree scene without the need of the pan-tilt-mechanism. In yet another alternative, image capture system 40 could comprise a cluster of imaging devices that communicate with computing device 14 using wired and/or wireless communications.

It is understood that image capture system 40 can comprise any type of one or more off-the-shelf and/or customized imaging devices. For example, image capture system 40 could comprise a sensitive, near-infrared to visible spectrum imaging device. In this case, the image data captured by image capture system 40 can be approximately one hundred times more sensitive in fog, haze, and dim light conditions as compared to a typical charge-coupled imaging device, thereby improving the accuracy of the measured visibility in all lighting and weather conditions. Further, image capture system 40 could comprise an infrared imaging device, an ultraviolet imaging device, etc. To this extent, the invention can be applied to measure visibility in a non-visible spectrum (e.g., ultraviolet spectrum) and/or information obtained from a non-visible spectrum can be correlated to measure visibility in the visible spectrum. Still further, image capture system 40 can comprise one or more filters that filter potential interference from other wavelengths of light that are not used in measuring the visibility from the image data. In this manner, the overall quality of the image data is improved. In one embodiment, image capture system 40 includes a filter system that comprises a 72 mm wavelength infrared filter that obtains a desired light spectrum for the image data captured by image capture system 40. In this case, the image data has an improved scene contrast and reduced shadow effects when compared with unfiltered image data. However, it is understood that this is only illustrative and various filters can be selected based on the particular imaging device and application.

In any event, image capture system 40 and/or computing device 14 can be remotely deployed. To this extent, image capture system 40 and/or computing device 14 each can be housed in a ruggedized protective enclosure that protects it from environmental effects such as wind, rain, dust, hail, snow, and the like. Additionally, the enclosure(s) and/or image capture system 40 can include component(s) to prevent fogging of the optics due to condensation and similar problems that can arise with a remotely deployed electronic device, an optical window cleaning mechanism, an optical window soot and defrosting mechanism, and/or the like. Further, the enclosure(s) can comprise one or more of: a rugged electronic packaging; a mounting system; a mounting and interface system for additional hardware (e.g., a weather sensor); a global positioning system (GPS) receiver; etc. Still further, it is understood that image capture system 40 and computing device 14 could be incorporated into a single enclosure, and the single enclosure could comprise a size and/or weight that renders it readily portable by an individual (e.g., the size of a handheld camera).

Regardless, the appropriate enclosure can be selected based on the location of the deployment. For example, image capture system 40 and/or computing device 14 could be mounted inside a window of a building, thereby requiring less protection from the elements. Alternatively, image capture system 40 and/or computing device 14 could be deployed on water (e.g., an ocean, lake, or the like), and appropriate protections and supports (e.g., piles, floatation, or the like) can be included. Similarly, image capture system 40 and/or computing device 14 can be deployed in extreme environments such as the arctic, at high altitude, under water, on an extra-terrestrial body, or the like, and appropriate protection can be included. Still further, image capture system 40 and/or computing device 14 could be deployed on a vehicle (e.g., an aircraft, automobile, etc.), to detect dangerous conditions and/or verify results of stationary systems. For example, when deployed on an aircraft, image capture system 40 could obtain images of the ground along the aircraft's path, verifying the visibility along the changing pathway.

As shown in FIG. 1, computing device 14 can be in communication with a remote system 42. To this extent, computing device 14 can communicate the measured visibility to remote system 42 and/or image data on which the measured visibility is based. Additionally, as discussed further herein, remote system 42 can enable a remote user (e.g., at an office) to adjust and/or control the operation of computing device 14 and/or image capture system 40. Remote system 42 can forward the measured visibility and/or image data on to one or more application systems 44A-D for various purposes. For example, remote system 42 can provide the measured visibility and/or image data to a media outlet 44A (e.g., a television or radio station), to another visibility measurement system 44B, to another remote system 44C for further processing and/or analysis, and/or to an archive system 44D, or the like, for storage for research or later reference.

Figure 2:
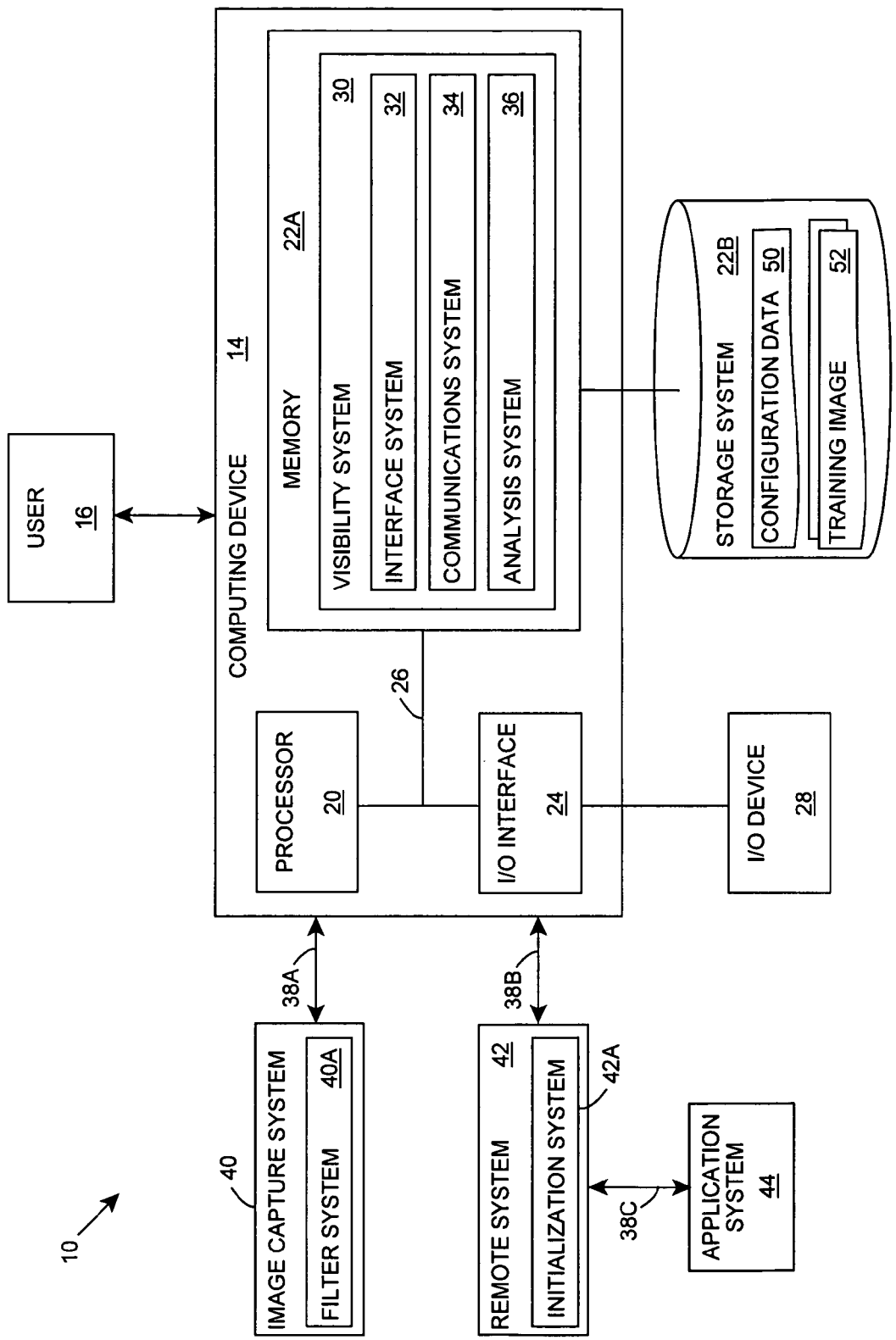
FIG. 2 shows a block diagram of the environment of FIG. 1.

Further details of environment 10 are shown and discussed with reference to FIG. 2, which shows a block diagram of the various systems in environment 10. To this extent, image capture system 40 is shown in communication with computing device 14. Computing device 14 is shown including a visibility system 30, which enables computing device 14 to measure visibility by performing the process steps of one embodiment of the invention.

Computing device 14 is shown including a processor 20, a memory 22A, an input/output (I/O) interface 24, and a bus 26. Further, computing device 14 is shown in communication with an external I/O device/resource 28 and a storage system 22B. As is known in the art, in general, processor 20 executes computer program code, such as visibility system 30, that is stored in memory 22A and/or storage system 22B. While executing computer program code, processor 20 can read and/or write data, such as configuration data 50, to/from memory 22A, storage system 22B, and/or I/O interface 24. Bus 26 provides a communications link between each of the components in computing device 14. I/O device 28 can comprise any device that enables user 16 to interact with computing device 14 or any device that enables computing device 14 to communicate with one or more other computing devices, such as image capture system 40 and/or remote system 42.

In any event, computing device 14 can comprise any general purpose computing article of manufacture capable of executing computer program code installed by a user 16. However, it is understood that computing device 14 and visibility system 30 are only representative of various possible equivalent computing devices that may perform the various process steps of the invention. To this extent, in other embodiments, computing device 14 can comprise any specific purpose computing article of manufacture comprising hardware and/or computer program code for performing specific functions, any computing article of manufacture that comprises a combination of specific purpose and general purpose hardware/software, or the like. In each case, the program code and hardware can be created using standard programming and engineering techniques, respectively.

For example, in one embodiment, application-specific integrated circuits (ASICs) are used to reduce the size, weight, and cost of computing device 14. In this case, processor 20 comprises a customized processing board designed to implement the process steps of the invention. To this extent, an open hardware platform, such as PC-104 based boards assembled and integrated in an enclosure, could be used. It is understood, however, that various alternatives are possible, including, for example, high performance embedded microcontrollers, custom imaging ASICs (e.g., Raptor II/III, Clarity III/IV, etc.), micro-controller/digital signal processing (DSP) combinations, etc.

Since computing device 14 may be remotely deployed, low power consumption, in addition to processing power (MIPS), may be an important consideration in the selection and design of the various components of computing device 14. To this extent, a high performance power supply, such as a twelve volt direct current power supply, can be included and be periodically charged using, for example, a solar cell. However, it is understood that power can be supplied using any solution, including obtaining power from a line source, utilizing a fuel cell or engine to generate power, or the like.

Additionally, the hardware design of computing device 14 can include one or more of various power-saving features and innovations. These can include one or more of: component selection based on low power consumption (e.g., use of Elan Sc-400 over Intel Pentium II); use of lowest possible main power rails (e.g., three volts); use of lowest possible clock speed and/or clock speed adjustment (e.g., via CLKRUN in peripheral component interconnect (PCI) bus-based design); tie up all unused gates; power conscious circuit board design (e.g., lower capacitance via shorter runs); avoidance of mixed mode designs (e.g., three volt and five volt designs); use of distributed power delivery system via multiple power regulators closer to the subsystems and controllable via software/hardware; use of solid-state power switches to control power to parts of the system where a control gate may not be provided; use of tri-state rather than shutting off a device; use of low drop power regulators; reduce headroom by the selection of battery voltage close to the final system voltage requirements; use of interrupt driven I/O over polled I/O (e.g., keyboard matrix encoder instead of polling); use of gas gage with battery pack to monitor the pack; use of bus monitoring chip that ties in with the processor; etc.

Similarly, the software design of computing device 14 can assist in power conservation, such as: embedding power save features in device drivers and main system control software via predetermined power usage states (e.g., turn off sections of hardware when not in use); use of code speed up methods for speedier code that saves power (e.g., avoid multiple transfers between buffers when an image processing algorithm can operate on the final storage buffer); etc. Further, one or more system-level design approaches can be used to conserve power, including, for example: use of buffering to store information when I/O levels are mismatched between devices; turn storage devices off (e.g., a burst mode data transfer to transfer data from memory 22A to an external storage system 22B, such as a PCMCIA card); throttle down processor 20 when lower performance is required; create a self-learning kernel to disable infrequently used portions of the system; incorporate a master system shut off power switch using a user-programmable shut off timer; incorporate a master system suspend mode using a user-programmable suspend time; enable both a maximum speed and a maximum battery life mode; incorporate a fuzzy logic embedded controller to control system level power distribution, processor frequency, fan control, and the like; etc. It is understood, however, that the incorporation of power-saving features needs to be balanced with user irritation factors and delays, over complication, diminishing returns, etc. To this extent, the design can be prioritized using the 80-20 principle.

As mentioned previously, computing device 14 communicates with image capture system 40 and remote system 42 over one or more communications links 38A-B. Similarly, remote system 42 communicates with application system 44 over a communications link 38C. Communications links 38A-C each can comprise any combination of various types of communications links as is known in the art. To this extent, each communications link 38A-C can comprise any combination of wireless and/or wired communications links that include any combination of public and/or private networks.

In one embodiment, computing device 14 includes various communications systems, including RS-232, a telephone, a wireless telephone, a radio link, and an Internet interface. RS-232 communications can be supported directly by an embedded processor that translates the logic levels to the RS-232 levels, which does not require an external twelve volt power supply, thereby saving power. A telephone/wireless telephone interface can comprise a low baud rate, e.g., 2400-baud, modem. For radio frequency (RF) communication, computing device 14 can comprise a 410 MHz or a 900 MHz connectivity that is NOAA RF band compatible. The Internet interface can comprise a direct interface that does not require implementation of a TCP/IP stack in the main embedded controller. It is understood that any combination of various types of communications systems can be implemented, such as one-to-one cable connections, a cellular phone link, a satellite modem, a wireless modem, a standard telephone line, etc. In any event, wired communications can be implemented over a dedicated line and/or one or more public communication networks. Further, when various types of interfaces are included, communications can use a flexible communications stack. Such a stack can support modem style commands, TCP/IP, packet handling, SDI-12, multiple baud rates, etc.

In communicating data over one or more of the communications links 38A-C, it may be desirable to reduce the bandwidth required to complete the communications. To this extent, one or more compression routines can be used to compress the image data. The compression can comprise any compression solution, including a lossless compression (e.g., Huffman coding) and/or a lossy compression (e.g., wavelet encoding, region of interest). Further, any encryption solution can be implemented to encrypt the data being transmitted if security is a concern.

As previously mentioned and discussed further below, visibility system 30 enables a computing infrastructure, such as computing device 14, to measure visibility. To this extent, visibility system 30 is shown including an interface system 32 for interfacing with user 16, a communications system 34 for communicating with image capture system 40 and remote system 42, and an analysis system 36 for analyzing image data to measure the visibility. Additionally, image capture system 40 is shown including a filter system 40A, which can comprise one or more filters as discussed above, and remote system 42 is shown including an initialization system 42A for initializing the operation of analysis system 36. Operation of each of these systems is discussed further below. However, it is understood that some of the various systems shown in FIG. 2 can be implemented independently, combined, and/or stored in memory for one or more separate computing devices that are included in a computer infrastructure. For example, initialization system 42A could be included in computing device 14 and/or visibility system 30 could be included in remote system 42. In the former case, computing device 14 could be implemented without any communication with a remote system 42 and/or application system 44. In the latter case, all processing of the image data can be performed remotely from image capture system 40. Further, it is understood that some of the systems and/or functionality may not be implemented, or additional systems and/or functionality may be included as part of environment 10.

In any event, the invention measures visibility based on a set (one or more) of images. FIG. 3 shows illustrative method steps that can be performed according to one embodiment of the invention, which will be discussed in conjunction with environment 10 of FIG. 2. In step S1 of FIG. 3, a field of view for measuring the visibility is selected. In one embodiment, user 16 can select and set up image capture system 40 at a location and/or direction that will result in a captured image that is rich in features (e.g., buildings, permanent landmarks, etc.). For improved operation, it is preferable that the features remain relatively constant over large periods of time. To this extent, the features should not be prone to seasonal changes (e.g., leaves falling, snow accumulation). Regardless, user 16 could use initialization system 42A to set up an appropriate angle, zoom, or the like for image capture system 40 so that the field of view includes sufficient detail of the various features while reducing an amount of the field of view that is not helpful in measuring visibility (e.g., due to changing features, lack of features).

In step S2, initialization system 42A identifies a set (one or more) of portions of an image having the selected field of view. The portion(s) of the image are used when measuring the visibility. In one embodiment, initialization system 42A identifies a set (one or more) of "patches" in the image. Each patch comprises a region of interest within the image that will be used in measuring the visibility. Consequently, each patch can be selected based on the presence of a plurality of features that will be useful in measuring visibility. To this extent, each patch should include multiple features (e.g., edges, grooves, lights, etc., formed by windows on a building, poles, intricate buildings, etc.) that are not prone to temporary and/or seasonal changes (e.g., snow, passing vehicles, etc.) that would substantially alter image data for the patch. In an alternative embodiment, initialization system 42A can identify specific target objects within the image for the set of portions. For example, initialization system 42A could select a bridge, a building, a set of poles on a bridge, etc., which are used when measuring the visibility. Various other embodiments are also possible. However, for clarity the discussion herein uses patches as an illustrative example. Regardless, it is readily apparent that the process equally applies to these other alternatives.

Figure 4A:
FIGS. 4A-B show illustrative sets of patches that could be selected for an image obtained during the day and night, respectively.
Figure 4B:

In general, the features for an image obtained during the day may be different from the features for an image obtained during the night. For example, building edges can be useful features during the day, but may not be available in an image obtained during the night. Similarly, light emitted from windows of a building or a street light may be useful features during the night, but may not be available in an image obtained during the day. To this extent, initialization system 42A can identify multiple sets of portions of the image (e.g., patches) for use in different lighting conditions. In particular, initialization system 42A identify a first set of patches for use during the day and a second set of patches for use during the night. For example, FIG. 4A shows an illustrative set of patches P1-P9 that could be selected for an image 54A obtained during the day, while FIG. 4B shows an illustrative set of patches P10-P15 that could be selected for an image 54B obtained during the night. As can be seen, both images 54A-B comprise the same field of view, however, the respective sets of patches differ substantially. Each patch P1-15 should include multiple features. To this extent, for patches P10-P15, multiple sources of light should be included to reduce the impact of one or more light sources being turned off. However, it is understood that this need not be the case, and an identical set of patches could be used for both day and night images when appropriate.

Returning to FIGS. 2 and 3, initialization system 42A can identify patches based on the distance of the corresponding features from image capture system 40. In particular, the features found in each patch can be roughly the same distance from image capture system 40. Since the visibility of a feature is dependent on its distance from image capture system 40, the processing of the patch described herein will not be skewed by data for some features within a patch being a substantially different distance from image capture system 40 than other features.

Additionally, initialization system 42A can identify the set of patches so that it includes patches that correspond to various distances from image capture system 40. For example, initialization system 42A can identify a plurality of zones within the field of view. Each zone can comprise a unique range of distances from image capture system 40 that is defined by a near distance and a far distance. Subsequently, at least one patch can be selected for each of the plurality of zones. In general, each patch should have most, if not all, features of interest present within the particular zone.

In one embodiment, a user 16 utilizes initialization system 42A to select the set of patches. For example, user 16 can use initialization system 42A to generate a request that image capture system 40 capture an image. The request can be received by interface system 32, which can instruct image capture system 40 to capture the image. The captured image can be received by interface system 32, and communications system 34 can communicate the image for use by remote system 42. Once received, user 16 can use initialization system 42A to selectively identify a region for each patch. Alternatively, initialization system 42A can comprise an image-processing suite that automatically selects the set of patches based on automatically determined distances and/or an analysis of features. In particular, initialization system 42A can perform image processing to automatically identify a plurality of zones in the image. Additionally, initialization system 42A can automatically select patches based on the features present and/or zone in which the features are located. To this extent, initialization system 42A could obtain geographic information system (GIS) data to accurately evaluate the distances for the various patches. For example, initialization system 42A could match the image with a stored GIS map of the area, localize image capture system 40 using the global positioning system (GPS) or the like, etc., to accurately evaluate the distances. Further, when image capture system 40 is deployed on a vehicle or the like, initialization system 42A can dynamically update the identified patches based on, for example, known features obtained from GIS data, or the like.

In either case, information corresponding to each patch P1-P15 (FIGS. 4A-B) is provided as configuration data 50 for use in measuring the visibility. To this extent, the information can comprise the image coordinates, width, and height of a rectangle defining each patch, a distance from image capture system 40 for each patch, a day/night/both indication for the patch, and the like. Further, any relative weight for each patch, an indication of the field of view (when multiple images with differing fields of view are used), and other related data can be associated with each patch and stored as configuration data 50. While shown and discussed as being rectangular, it is understood that each patch can comprise any desired shape.

In step S3 of FIG. 3, interface system 32 obtains an image from image capture system 40. In one embodiment, interface system 32 can request that image capture system 40 capture an image and provide it to interface system 32. Alternatively, image capture system 40 can periodically provide images to interface system 32 for processing. In the latter case, image capture system 40 could comprise a video recording device or the like that sends a continuous stream of images for processing by visibility system 30. In either case, as discussed above, image capture system 40 can comprise a filter system 40A that filters undesired wavelengths of light from the image, which can be based on light having a wavelength in any desired spectrum(s). For example, in one embodiment, image capture system 40 captures images based on light in the visible and near-infrared spectrums.

Subsequently, visibility system 30 measures visibility based on the image. In measuring the visibility, visibility system 30 can adjust how it estimates the visibility based on the lighting condition for the image. To this extent, in step S4, analysis system 36 can determine a lighting condition for the image. In one embodiment, analysis system 36 can initially assume a particular lighting condition based on a time of day obtained from a clock or the like maintained by computing device 14. Additionally, analysis system 36 can use the lighting condition that was determined for a previous image taken within a relatively short time period (e.g., thirty seconds). Further, analysis system 36 can analyze the image to determine a lighting condition. For example, patch P1 (FIG. 4) can correspond to the sky in a portion of the image. In this case, analysis system 36 can analyze an intensity of patch P1 to determine if the lighting condition (e.g., daytime, nighttime, diurnal).

In any event, in step S5, analysis system 36 calculates a set (one or more) of metrics for the image. In particular, analysis system 36 can select a set of portions of the image (e.g., patches) and/or a set of metrics based on the lighting condition for the image. Using the image data for each patch, analysis system 36 can calculate the set of metrics for each patch. In one embodiment, multiple metrics are calculated for each patch. The use of multiple metrics provides a visibility measurement that is more accurate and less susceptible to error due to a particular lighting condition. Further, each metric can be selected such that it changes monotonically with decreasing visibility. This makes each metric a clear, elegant indicator of visibility. When multiple metrics are used, other metrics can compensate for the weakness of one or more metrics to render an accurate visibility measurement. An illustrative set of metrics is now discussed in further detail. However, it is understood that the invention is not limited to the use of all or some of the metrics discussed herein.

Figure 5B:
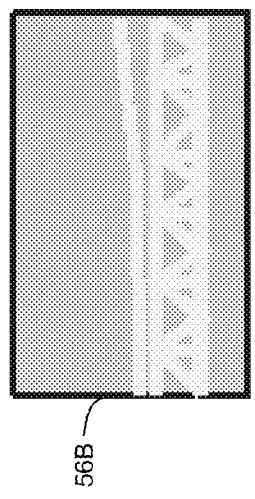
FIGS. 5A-B show an illustrative high visibility image and low visibility image, respectively, that are based on the same patch.
Figure 5A:
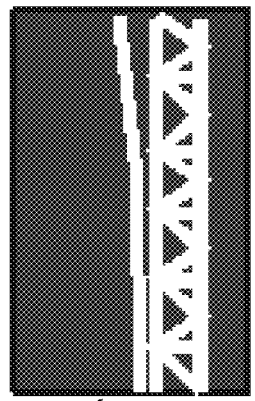

One subset of metrics can be based on the pixel intensity for the image data for each patch. In one embodiment, a mean pixel intensity metric and/or a mode pixel intensity metric are calculated. In general, when visibility is high, the mean and/or mode for the pixel intensity will be relatively low. However, when visibility is low due to haze, fog, precipitation, or the like, the mean and/or mode for the pixel intensity will be relatively high since any light (day or night) will be scattered by the particles. For example, FIG. 5A shows an illustrative high visibility image 56A based on patch P2 (FIG. 4A), while FIG. 5B shows an illustrative low visibility image 56B corresponding to the same patch P2. As can be seen in FIGS. 5A-B, many pixels in image 56A have a relatively low pixel intensity, thereby making the mean and/or mode for image 56A lower than that of image 56B.

Figure 6B:
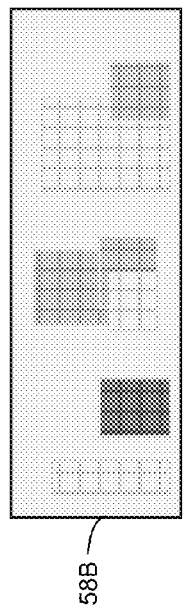
FIGS. 6A-B show an illustrative high visibility image and low visibility image, respectively.
Figure 6A:
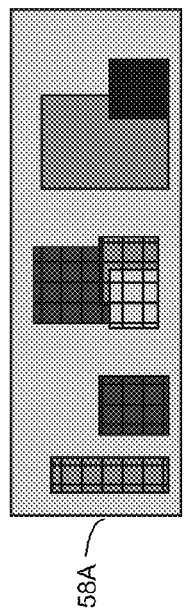

Additionally, analysis system 36 can calculate a standard deviation of the pixel intensities for each patch. In general, when features of a target object and/or light sources are concealed by particles (e.g., haze, fog, etc.), the standard deviation of the pixel intensities will become lower. For example, FIG. 6A shows an illustrative high visibility image 58A while FIG. 6B shows an illustrative low visibility image 58B. In this case, the pixel intensities of image 58A comprise a standard deviation of approximately 0.15, while the pixel intensities of image 58B comprise a standard deviation of approximately 0.1. To this extent, a relatively high standard deviation metric will indicate high visibility, while a relatively low standard deviation metric will indicate low visibility. Further, to make the standard deviation metric more robust against diurnal effects, analysis system 36 can divide the calculated standard deviation by the mean pixel intensity. As a result, the pixel intensity subset of metrics provides some indication of the presence of such visibility-limiting factors as haze, fog, precipitation, and the like.

Figure 7B:
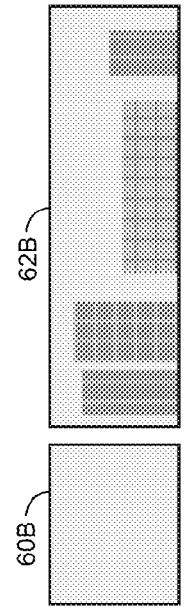
FIGS. 7A-B each show an illustrative sky patch and corresponding target object patch pair during high and low visibility, respectively.
Figure 7A:
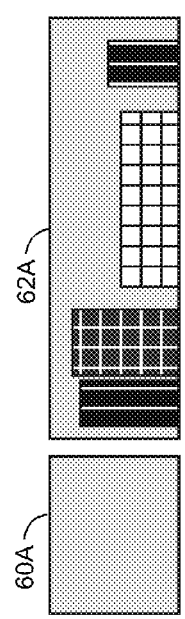

Another subset of metrics can be based on a contrast between a target object and a background for the target object. In general, as visibility decreases, the contrast will decrease. The contrast can be calculated, for example, as a ratio that comprises: (luminance of background-luminance of target object)/luminance of background. In one embodiment, a particular patch can be selected and designated as the background patch. For example, the patch could comprise a background for the target objects. However, such a selection could be susceptible to a background cover-up effect, in which a fog could interpose itself between the object and the background, thereby artificially raising the brightness of the background. Alternatively, the patch can comprise an area of the image that corresponds to the sky, e.g., patch P1 of FIG. 4A. In either case, the mean and/or mode of the pixel intensity can be used to measure the luminance of each patch (i.e., for the target object and for the background). For example, FIG. 7A shows a sky patch 60A and corresponding target object patch 62A during high visibility while FIG. 7B shows the same sky patch 60B and corresponding target object patch 62B during low visibility. As can be seen, sky patch 60B is noticeably lighter than sky patch 60A, and the same lightening and fading of contrast can be seen between target object patches 62A and 62B. This results in a lower contrast for target object patch 62B with respect to target object patch 62A.

In one embodiment, the contrast subset of metrics is only used to analyze daytime images since, for nighttime images, the background and foreground substantially include darkness and lights with little variation except a generalized lightening/darkening of the background based on the variation of the visibility. However, with the use of a more sensitive image capture system 40 and/or images based on non-visible radiation, the contrast subset of metrics may be used for all images.

Another subset of metrics for each patch can be based on edges. In order to locate edges within a particular patch, one or more edge detection solutions can be used. For example, analysis system 36 can calculate a first edge metric using Laplacian of Gaussian edge detection and calculate a second edge metric using Sobel edge detection. In either case, the edge metric can be based on a pixel count. For example, the edge-detected patch can be converted into a binary image using a suitable threshold, e.g., 0.001 for Laplacian of Gaussian edge detection and 0.0075 for Sobel edge detection. The binary image can comprise white pixels that correspond to each detected edge, and a count of the number of white pixels can comprise the edge metric.

Figure 8B:
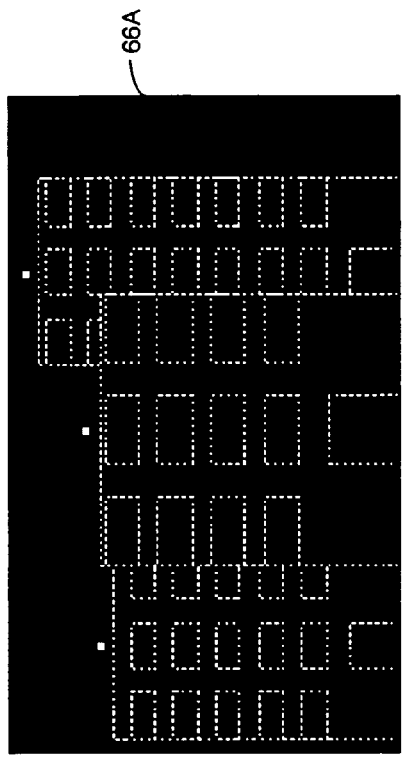
FIGS. 8A-B show an illustrative high visibility image and resulting binary image, respectively.
Figure 9B:
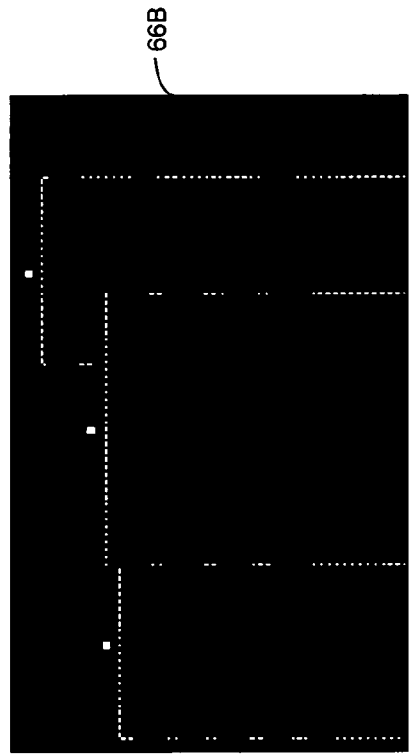
FIGS. 9A-B show an illustrative low visibility image and resulting binary image, respectively.
Figure 8A:
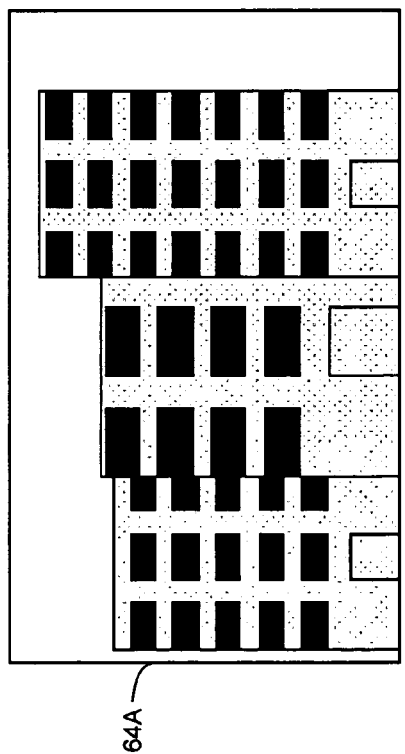
Figure 9A:
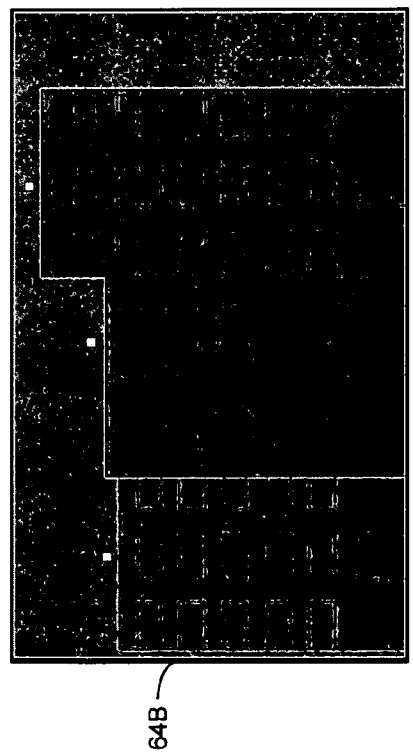

In general, as visibility decreases, the edges in the patch become blurred and fewer edges, and therefore white pixels, will be detected. To this extent, FIG. 8A shows a high visibility image 64B while FIG. 9A shows a corresponding low visibility image 64B for the same patch. After detecting the edges and converting the respective images 64A-B to binary images, FIG. 8B shows the resulting binary image 66A for image 64A while FIG. 9B shows the resulting binary image 66B for image 64B. As can be seen, the number of white pixels for binary image 66A (high visibility) will be higher than the number of white pixels for binary image 66B (low visibility).

Figure 10A:
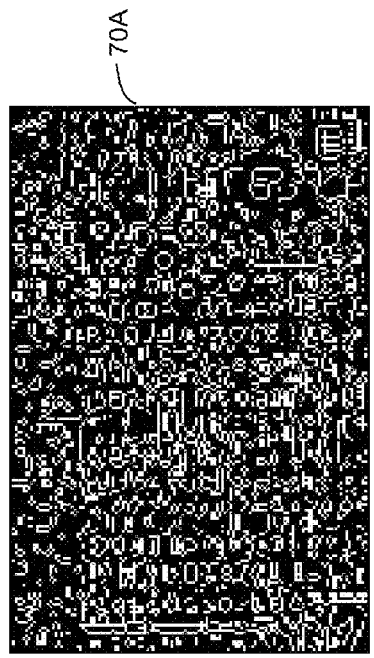
FIGS. 10A-B show an illustrative high visibility nighttime image and resulting binary image, respectively.
Figure 11A:
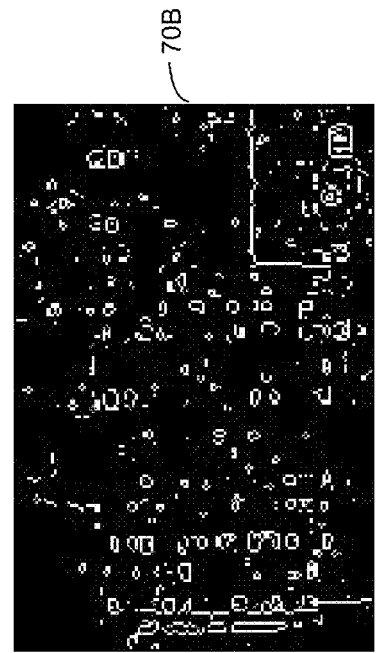
FIGS. 11A-B show an illustrative low visibility nighttime image and resulting binary image, respectively.
Figure 10B:
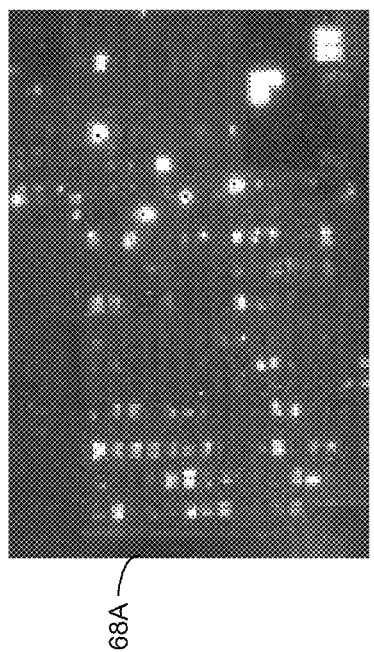
Figure 11B:
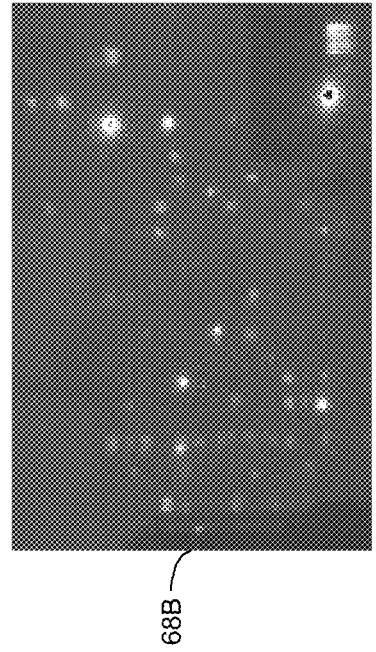

The subset of edge metrics also provide a useful result for nighttime images. In a nighttime image, each "edge" comprises an apparent boundary of brightness, e.g., where the light ends, rather than an edge of a target object. As with a daytime image, low visibility blurs the edges, rendering fewer of them distinguishable, thereby lowering the resulting edge metric. For example, FIG. 10A shows a high visibility nighttime image 68A while FIG. 11A shows a corresponding low visibility nighttime image 68B for the same patch. After detecting the edges and converting the respective images 68A-B to binary images, FIG. 10B shows the resulting binary image 70A for image 68A while FIG. 11B shows the resulting binary image 70B for image 68B. In the high visibility binary image 70A, several edges corresponding to illuminated portions of buildings are detected. In contrast, the low visibility binary image 70B primarily comprises only edges that can be attributed to a particular light source. Consequently, as with the daytime images, the high visibility binary image 70A has a higher number of white pixels than the low visibility binary image 70B.

Still another subset of metrics can be based on a frequency transform for each patch. The subset of frequency transform metrics analyze the fraction of effective image "energy" present in particular frequency components. In one embodiment, analysis system 36 calculates a discrete cosine transform of each patch. For example, F(m,n) can denote the discrete cosine transform, with m and n varying over the dimensions of the patch. The total energy, E, can be calculated as:

$$E = \sum_m \sum_n \|F(m, n)\|^2$$

In this case, analysis system 36 can calculate an energy fraction in non-zero frequencies metric, $M_1$, as:

$$M_1 = \frac{E - \|F(1, 1)\|^2}{E}.$$

Further, analysis system 36 can calculate an energy-weighted average frequency metric, $M_2$, as:

$$M_2 = \frac{1}{E} \sum_m \sum_n \|F(m, n)\|^2 \sqrt{m^2 + n^2}.$$

Figure 12A:
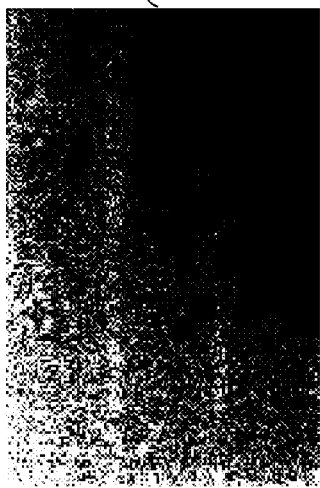
FIGS. 12A-B show an illustrative high visibility image and corresponding graph of the discrete cosine transform, respectively.
Figure 12B:
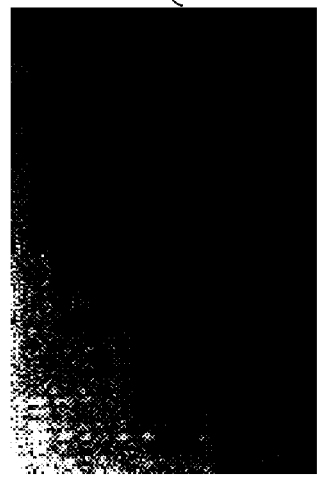
Figure 13A:
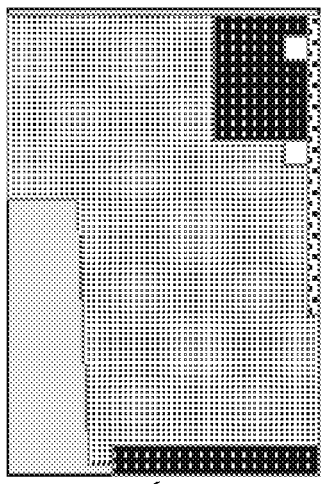
FIGS. 13A-B show an illustrative low visibility image and corresponding graph of the discrete cosine transform, respectively.
Figure 13B:
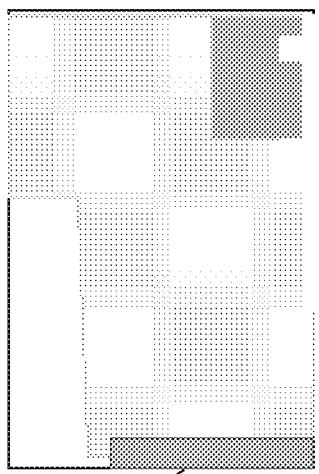

In general, as an image becomes blurry due to low visibility, the high frequency information in the image decreases and the frequency transform metrics will also decrease. For example, FIG. 12A shows an illustrative high visibility (clear) image 72A and FIG. 13A shows an illustrative low visibility (hazy) image 72B for the same patch. FIG. 12B shows an illustrative graph of the discrete cosine transform 74A that corresponds to image 72A and FIG. 13B shows an illustrative graph 74B that corresponds to image 72B. In graphs 74A-B, the horizontal axis represents the horizontal frequencies and the vertical axis represents the vertical frequencies. Each pixel represents a distinct pair of frequencies, with the top left corner representing the zero frequency (i.e., mean intensity). The frequency increases in the right and downward directions. The intensity of the pixel represents the strength of the corresponding frequency in the respective image 72A-B. Consequently, the more pixels in the original image 72A-B whose frequencies depart from the mean, the higher the metric will be. To this extent, as illustrated by FIGS. 12A-B and 13A-B, more of these pixels are present in high visibility (e.g., clear conditions) than in low visibility (e.g., hazy conditions).

An additional subset of metrics can be based on a wavelet transform of each patch. Wavelet transforms are frequently used in compression. In general, a wavelet transform separates an image into various components of general features or approximations and detail features. In one embodiment, analysis system 36 calculates a two-dimensional wavelet transform of each patch. In this case, four coefficient matrices are generated; an approximation coefficient matrix, a horizontal detail coefficient matrix, a vertical detail coefficient matrix, and a diagonal detail coefficient matrix. Subsequently, analysis system 36 can reconstruct an approximation image, a horizontal detail image, a vertical detail image, and a diagonal detail image based on the corresponding matrices. Further, analysis system 36 can construct an overall detail image by adding the horizontal detail image, vertical detail image and diagonal detail image.

Figure 14A:
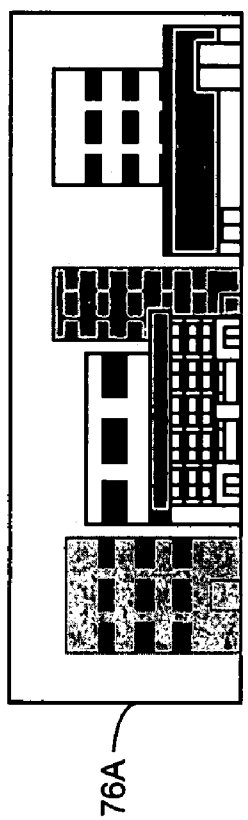
FIGS. 14A-C show an illustrative high visibility image and its corresponding approximation image and overall detail image, respectively.
Figure 14C:
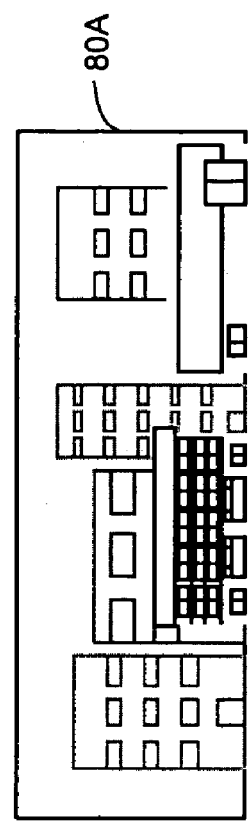
Figure 14B:
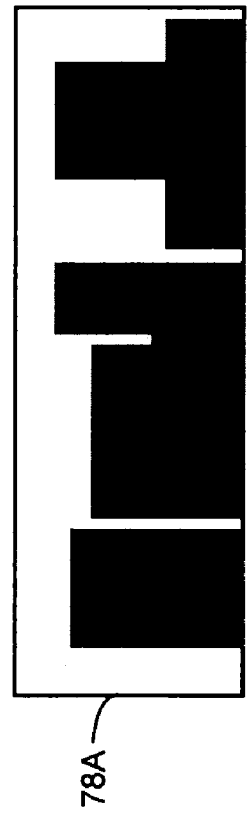
Figure 15A:
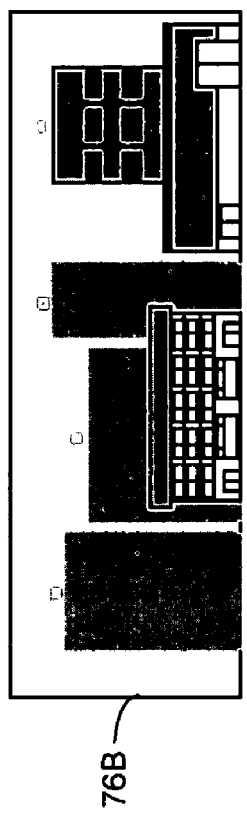
FIGS. 15A-C show an illustrative low visibility image and its corresponding approximation image and overall detail image, respectively.
Figure 15C:
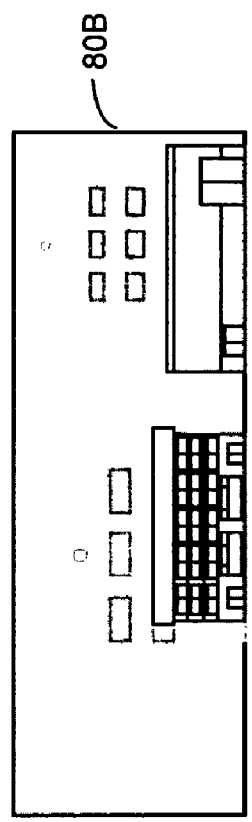
Figure 15B:
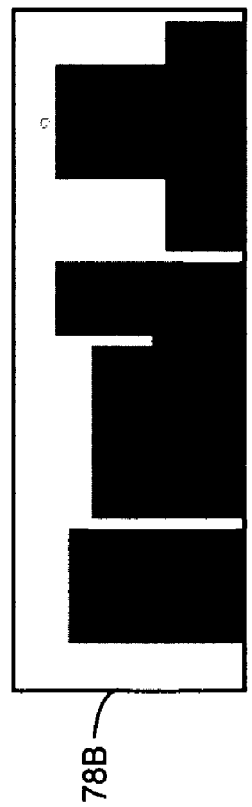

Analysis system 36 can then calculate one or more wavelet transform metrics based on the approximation image and overall detail image. For example, FIGS. 14A-C show an illustrative high visibility image 76A and its corresponding approximation ("low detail") image 78A and overall detail image 80A, while FIGS. 15A-C show an illustrative low visibility image 76B and its corresponding approximation image 78B and overall detail image 80B. Analysis system 36 can calculate a total energy of images 76A-B as a sum of the energies in the corresponding approximation image 78A-B and overall detail image 80A-B.

Using this information, analysis system 36 can calculate an energy fraction metric as a ratio of the energy in the overall detail image 80A-B to the total energy. Further, analysis system 36 can calculate a high-energy pixel count metric based on the overall detail image 80A-B. In this case, a threshold energy level can be selected, and a number of pixels exceeding the threshold energy level can be calculated. For example, the threshold energy level can comprise a percentage (e.g., 0.1%) of the total energy for the patch. For both the energy fraction metric and high-energy pixel count metric, a lower value will indicate a lower visibility.

Figure 16A:
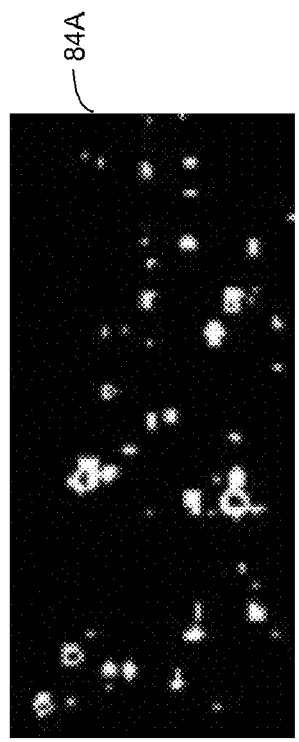
FIGS. 16A-B show an illustrative high visibility image and corresponding lamp count image, respectively.
Figure 17A:
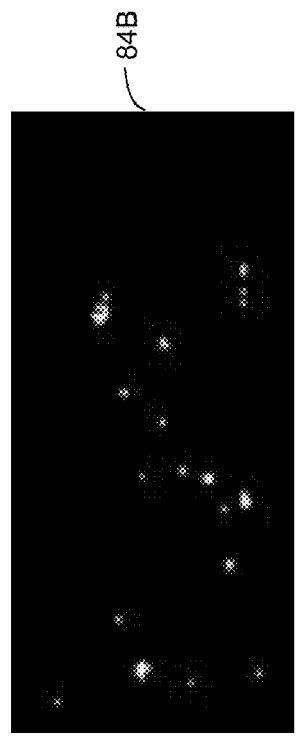
FIGS. 17A-B show an illustrative low visibility image and corresponding lamp count image, respectively.
Figure 16B:
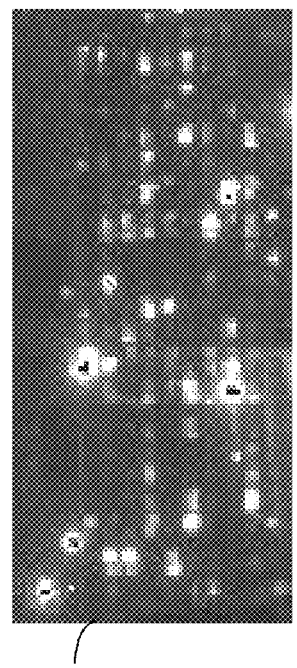
Figure 17B:
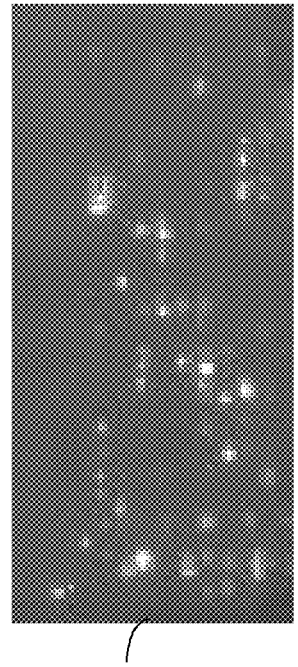

As noted previously, when measuring visibility based on a nighttime image, various attributes of artificial light sources can be used. To this extent, analysis system 36 can further calculate a lamp count metric for nighttime image data for each patch. In general, the lamp count metric is based on a number of light sources visible within the patch. On average, a number of stationary lights in a sufficiently large patch should be relatively constant. As a result, changes in the visibility will be the primary factor for noticeably affecting the lamp count metric. In operation, analysis system 36 can use a particular threshold to generate a lamp count image based on an original image. Subsequently, analysis system 36 can determine a number of light sources within the lamp count image. In one embodiment, initialization system 42A (FIG. 2) assigns a threshold to each patch, which can be based on an intensity of the light sources within the patch and stores the threshold along with the patch as configuration data 50 (FIG. 2). For example, FIGS. 16A and 17A show illustrative images 82A-B that respectively correspond to high visibility and low visibility conditions for a patch. FIGS. 16B and 17B show the corresponding lamp count images 84A-B, respectively. In this case, a lamp count based on lamp count image 84A would comprise sixty-two, while a lamp count based on lamp count image 84B would comprise thirty-one.

Since the lamp count metric is based on a number of artificial light sources, it is generally more effective in an urban/suburban environment where there are a substantial number of artificial light sources. However, the number of artificial light sources in these areas may vary based on the time. In order to provide additional accuracy, initialization system 42A (FIG. 2) can further track an average number of lamp counts obtained for a particular time period (e.g., each hour) during high visibility. Such tracking is especially useful when the target object comprises an apartment building or the like, which will generally have fewer light sources early in the morning (e.g., three AM) than in the evening (e.g., nine PM). Additionally, the tracking can be based on a day of the week, time of year, etc. In any event, the total lamp count obtained can be compared to a corresponding tracked lamp count for the particular time and/or day that the image was obtained. While discussed with reference to artificial light sources, it is understood that the lamp count could be implemented with natural light sources (e.g., moon, stars) in a location such as a rural area or the wilderness that lacks and/or has a limited number of artificial light sources. In this case, however, a more sensitive image capture system 40 (FIG. 2) may be required.

In general, all of the previous metrics can be calculated based on grayscale information for a particular image. To this extent, when an image comprises a color image, analysis system 36 can convert the image to its corresponding grayscale image for processing. However, in such a conversion, some information is lost from the original color image. For example, it is possible for two images that have entirely different colors to correspond to the same grayscale image. Further, as visibility decreases due to fog, precipitation, and the like, the colors in the resulting image become less prominent resulting in an image that appears more grayish. Consequently, analysis system 36 can further calculate a color metric.

In one embodiment, the color metric is based on the intensity of each pixel. For example, for a particular pixel (i, j), $R_{ij}$, $G_{ij}$, and $B_{ij}$ can denote the corresponding red, green, and blue color components, respectively. An intensity of the pixel can be calculated by:

$$I_{ij} = \frac{R_{ij} + G_{ij} + B_{ij}}{3}$$

and the color metric of a patch with M×N pixels ($M_p$) can be calculated by:

$$M_P = \frac{1}{MN} \sum_{i=1}^{M} \sum_{j=1}^{N} ((R_{ij} - I_{ij})^2 + (G_{ij} - I_{ij})^2 + (B_{ij} - I_{ij})^2)$$

In this case, as visibility decreases, the color metric will also decrease. When a patch is completely gray, its corresponding color metric will be zero.

The color metric has a significant advantage over grayscale-image based metrics. For example, on a clear day, a particular target object may be covered by a thin veil of smoke or fog. The veil will not be prominent in the grayscale image, and moreover, the features and edges of the target object may remain distinct in the grayscale image. Consequently, the grayscale-image based metrics would not likely detect the obscuring of the target object. However, such a veil would conceal the colors of the target object significantly, resulting in a sharp decrease of the color metric. In one embodiment, the color metric is only used in conjunction with images acquired during the day. However, image capture system 40 (FIG. 2) could comprise a sufficiently sensitive imaging device and be used in conjunction with light sources of differing colors in each patch (e.g., sodium yellow of a streetlamp versus the whiter color of an incandescent lamp), to enable the use of the color metric in nighttime images.

Returning to FIGS. 2 and 3, in step S6, analysis system 36 can calculate a visibility based on the set of metrics. To this extent, when the set of metrics includes several different metrics, such as those described above, analysis system 36 can combine these metrics and/or an estimated visibility for each metric using a weighted average. In this case, the various metrics can compensate for one or more weaknesses of any single metric to obtain an accurate and robust measurement of the visibility. However, for each patch, the variation as a function of the visual range differs for each metric. Similarly, for each metric, the variation as a function of the visual range differs for each patch. In general, for each metric-patch combination, a function that describes the variation as a function of the visual range is unknown. Additionally, the sensitivity to various diurnal factors such as time of day, shadows, position of sun, cloud cover, etc., which do not impact the visual range in the same proportion, varies among the metrics and metric-patch combinations. As a result, analysis system 36 lacks information that would be useful in combining and/or analyzing the metrics.

In one embodiment, analysis system 36 uses a plurality of techniques to estimate a visual range based on each of the set of metrics. Subsequently, analysis system 36 can combine the resulting visual range estimates to obtain the measured visibility for the image. Alternatively, analysis system 36 can use a single technique to measure the visibility for the image.

In one technique, analysis system 36 estimates a visual range using a "vis-curve" for each unique metric-patch combination. A vis-curve comprises a curve that describes the variation of a metric with the visual range for a particular patch. To this extent, configuration data 50 can comprise a set of vis-curves that includes a unique vis-curve for each possible metric-patch combination. Additionally, configuration data 50 can comprise a first set of vis-curves that correspond to daytime images for each metric-patch combination and a second set of vis-curves that correspond to nighttime images for each metric-patch combination. In this case, analysis system 36 will obtain a set of vis-curves based on the lighting condition for the image. For example, when the lighting condition comprises daytime, analysis system 36 obtains the set of daytime vis-curves, when the lighting condition comprises nighttime, analysis system 36 obtains the set of nighttime vis-curves, and when the lighting condition is diurnal, analysis system 36 can obtain both the set of nighttime vis-curves and set of daytime vis-curves and combine the results.

Figure 18:
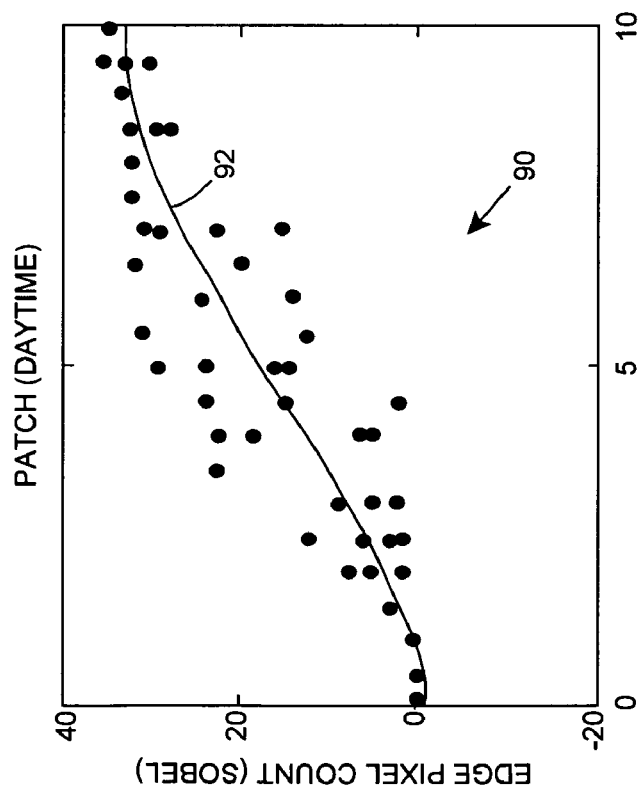
FIG. 18 shows an illustrative plot and corresponding vis-curve for a set of edge pixel count metric-daytime patch combinations.

The set of vis-curves can be generated based on the metrics of one or more pre-existing images (e.g., training images 52). In particular, initialization system 42A can plot the metric values for the particular metric-patch combination from all of the relevant (e.g., daytime or nighttime) training images 52 as a function of the visual range for each training image 52. Subsequently, initialization system 42A can fit a polynomial curve (e.g., of order three) to the plotted metric values and the resulting coefficient vector of the fitted polynomial can be stored as the vis-curve for the corresponding metric-patch combination. For example, FIG. 18 shows an illustrative plot 90 and corresponding vis-curve 92 for a set of Sobel edge pixel count metric-daytime patch (e.g., patch P6 of FIG. 4A) combinations.

In any event, for each metric-patch combination, analysis system 36 uses the corresponding vis-curve(s) to estimate the visual range. The estimated visual range comprises the range for which the vis-curve attains the same metric value. If the result using the vis-curve is outside of a minimum (e.g., zero) and a maximum visibility range, the estimated visual range can be set to the appropriate minimum/maximum value. Once all vis-curves and metric-patch combinations have been processed, analysis system 36 can combine the visual range estimates to obtain an estimate of the visual range for the technique.

In order to combine the visual range estimates, analysis system 36 can obtain a set of weights for the corresponding metric-patch combinations. To this extent, configuration data 50 can comprise a set of weights for daytime, nighttime, and diurnal lighting conditions. In each set of weights, the metric that performs well for the particular lighting condition is given a higher weight. The set of weights can be determined empirically. In this case, reliable metrics such as the edge metric, and patches having many features are given a higher weight. In any event, based on the lighting condition, analysis system 36 can obtain the corresponding set of weights and use it to combine the estimates of the visual range from the various metric-patch combinations to obtain an estimated visual range for the image.

Additionally, analysis system 36 can determine whether the estimated visual range is relatively high or relatively low. In general, for a high visual range, the vis-curves for patches located in distant zones have large slopes (and hence high sensitivity) while the vis-curves for patches located in near zones have near-zero slopes. However, for a low visual range, the vis-curves for patches located in near zones have large slopes while the vis-curves for patches located in distant zones have a near-zero slope. Consequently, if the estimated visual range is relatively high, analysis system 36 can re-compute the estimated visual range using only those patches located in far and middle zones. Conversely, when the estimated visual range is relatively low, analysis system 36 can re-compute the estimated visual range using only those patches located in near and middle zones.

In another technique, analysis system 36 can estimate a visual range based on a set of "scene-curves". A scene-curve comprises a plot of a particular metric as a function of distance from image capture system 40. In this technique, for each metric, analysis system 36 can plot a series of metric value-patch distance points. Subsequently, analysis system 36 can fit a polynomial (e.g., an order three polynomial) to the plotted points.

In calculating a visual range for a particular metric, analysis system 36 can compare the fitted polynomial to a set of training scene-curves stored in configuration data 50. Each training scene-curve can comprise a corresponding estimated visual range. Analysis system 36 can determine the training scene-curve that is the best match for the fitted polynomial. The determination can be based on a distance between the two curves, which can be computed as the sum of the squares of the difference between the values of the two curves. In any event, analysis system 36 can then use the visual range that corresponds to the matched training scene-curve as the estimated visual range for the metric. As with the vis-curves described above, analysis system 36 can select a set of training scene-curves based on a lighting condition (e.g., daytime, nighttime, diurnal). Additionally, the estimated visual ranges for each metric are combined using a set of weights in the same manner discussed above with reference to the vis-curves to obtain an estimated visual range for the image.

Figure 19:
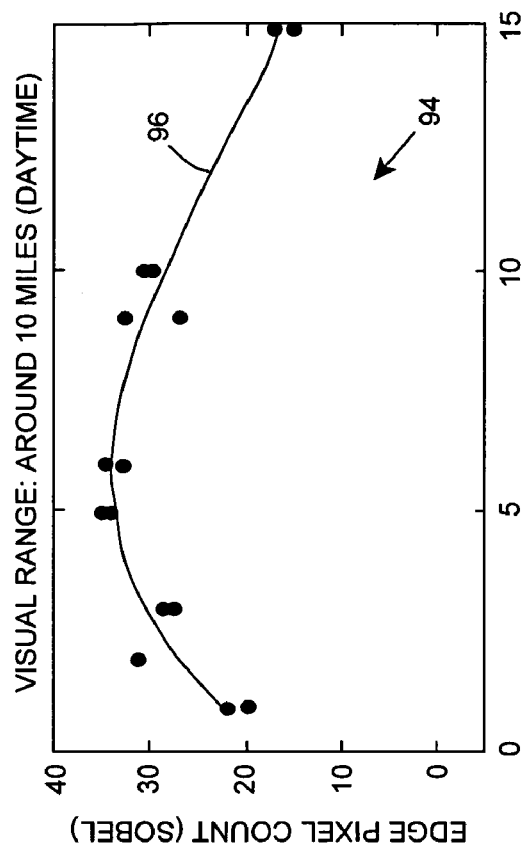
FIG. 19 shows an illustrative plot and corresponding scene curve for a set of edge pixel count metric-ten mile daytime visual range combinations.

The set of training scene curves can be based on a set of pre-existing images (e.g., training images 52). To this extent, initialization system 42A can select a set of visual range values that are within a window of possible visual range values from the visual range data for the training images 52. Subsequently, initialization system 42A can group the set of training images 52 according to the corresponding visual ranges and compute a scene-curve for every metric-visual range combination. In particular, initialization system 42A can plot a metric value for each patch in each training image 52 having a particular visual range as a function of the patch distance, and fit a polynomial curve (e.g., of order three) to the plotted points. The coefficient vector of the fitted curve is the scene-curve for the particular metric-visual range combination and can be stored in configuration data 50. For example, FIG. 19 shows an illustrative plot 94 and corresponding scene curve 96 for a set of Sobel edge pixel count metric-ten mile visual range (daytime) combinations.

In one embodiment, analysis system 36 combines the estimated visual range calculated based on the vis-curves with the estimated visual range calculated based on the scene-curves to obtain the measured visibility. For example, the two values could be averaged with equal weight. However, it is understood that this is only illustrative. To this extent, only one of the techniques could be used and/or other possible techniques could be used to obtain an estimated visual range for the image.

For example, in another technique, each image can comprise a large number (e.g., twenty to forty) of patches, each of which has a corresponding patch distance. For each metric-patch combination, initialization system 42A can determine a threshold value that comprises the metric value at which that corresponding patch is considered barely visible. Initialization system 42A can store the threshold values as configuration data 50. Subsequently, analysis system 36 can calculate a metric value for each metric-patch combination, and the metrics for each patch can be combined (e.g., using a corresponding set of weights) to determine if the patch is considered visible. Once all patches have been processed, analysis system 36 can estimate the visible range by finding the most distant patch that is considered visible.

In any event, once analysis system 36 has measured the visibility, communications system 34 can provide the visibility for use on remote system 42. As described above, remote system 42 can further provide the visibility to one or more application systems 44 for further processing and/or storage.

Returning to FIG. 2, as discussed above, analysis system 36 uses various configuration data 50 to measure the visibility based on an image. In one embodiment, some or all of configuration data 50 is based on a set (one or more) of training images 52. Further, the set of training images 52 can be updated using one or more previously processed images. In this manner, operation of visibility system 30 can adapt to changes in the field of view, and "learn" from previous images and their corresponding visibilities.

For example, when image capture system 40 and/or computing device 14 are deployed to a new location, no training images 52 will be available. In one embodiment, a set of training images 52 and corresponding configuration data 50 is provided for operation. For example, the set of training images could be obtained from a previously deployed image capture system 40 and computing device 14. Alternatively, the set of training images 52 and configuration data 50 can be generated as visibility system 30 operates over time.

In the latter case, image capture system 40 can capture a first training image 52, preferably when visibility is high (e.g., seven or more miles). Using initialization system 42A and/or interface system 32, user 16 can select a set of patches, estimate a distance for each patch, and estimate a visual range for the image. Alternatively, initialization system 42A can automatically select a set of patches and corresponding distances using image processing techniques. Regardless, this information can be stored as configuration data 50. Further, initialization system 42A can calculate an initial set of vis-curves for each metric-patch combination. In this case, since configuration data 50 for only a single image is available, the vis-curves can be calculated using a straight line having a predetermined slope (e.g., based on information from one or more other deployments and/or experimentation scenarios).

Additionally, the set of scene-curves will include only a single scene-curve for the visual range for the first training image 52. This process can be repeated for both a daytime as well as a nighttime lighting condition.

In any event, analysis system 36 can use configuration data 50 to begin measuring visibility for images received from image capture system 40. After the visibility has been measured for a particular image, analysis system 36 can further compare the image to the set of training images 52. Analysis system 36 can use any solution for comparing an image with the set of training images 52. For example, image data for one or more patches could be compared to image data for the same one or more patches in the set of training images 52. Alternatively, one or more of the set of metrics and/or the measured visibility could be compared with those for the set of training images 52.

When the newly processed image is sufficiently unique from all other images in the set of training images 52, initialization system 42A can add the new image to the set of training images 52 and/or update configuration data 50 based on the new image. To this extent, initialization system 42A can use the set of metrics for the new image together with the existing metric data for the set of training images 52 to update/modify one or more of the sets of vis-curves, the sets of scene-curves, the sets of weights, and the like. The set of training images 52 and corresponding configuration data 50 can be continually updated in this manner while computing device 14 and image capture system 40 are deployed at a site.

In general, over time, the set of training images 52 and configuration data 50 should stabilize. However, should the field of view change significantly (e.g., change of season, fire, construction, etc.), new images will again start to be added to the set of training images 52. Additionally, in order to ensure that analysis system 36 remains responsive to gradual changes to the field of view (e.g., trees growing), a training image 52 can be periodically removed from the set of training images 52 after a predetermined period of time (e.g., two years).

Periodically, a user 26 at remote system 42 could request that communications system 34 provide the set of training images 52 and/or corresponding configuration data 50 to remote system 42. In response, communications system 34 can provide the set of training images 52 and/or configuration data 50 for use on remote system 42. User 16 could then use initialization system 42A to review the set of training images 52 and/or configuration data 50 and make any necessary modifications. For example, user 16 could adjust a visual range estimate that corresponds to one or more of the set of training images 52, delete a training image 52, add a training image and corresponding configuration data 50, etc. Subsequently, remote system 42 can provide the updated set of training images 52 and/or configuration data 50 to computing device 14. After receiving the updated set of training images 52 and/or configuration data 50, visibility system 30 can update some or all of the configuration data 50 (e.g., sets of vis-curves, sets of scene-curves, etc.) using the updated data. Alternatively, initialization system 42A can update the necessary configuration data 50 before communicating it to computing device 14.

When the set of training images 52 comprises multiple training images, the sets of vis-curves and sets of scene-curves can be generated using a polynomial curve fitting. To this extent, when the set of training images 52 and/or configuration data 50 has been modified, initialization system 42A can generate a new vis-curve for each metric-patch combination that may be impacted by the modification as discussed above. Similarly, initialization system 42A can generate a new scene-curve for each metric-visual range combination that may be impacted by the modification as discussed above.

As noted previously, analysis system 36 can utilize a set of weights, e.g., multipliers, to determine how much influence any given metric has on a visibility measurement, thereby tailoring the accuracy and robustness of the final visibility measurements. To this extent, initialization system 42A can derive the set of weights in any number of ways including, for example, direct experimental evidence of performance as evaluated by an individual skilled in the art, comparison of the curves of the metrics to arrive at desirable curve characteristics (e.g., monotone, sensitivity (high slope), approach to linearity, low deviation, and the like) for each measurement condition and/or scenario (daytime, nighttime, diurnal, low visibility, high visibility, etc.). In one embodiment, initialization system 42A derives the set of weights through both experimentation and curve modeling and comparison.

In addition to measuring visibility, analysis system 36 and/or remote system 42 could further assess a situation based on the visibility measurement. For example, analysis system 36 and/or remote system 42 could detect poor visibility on a roadway, observe conditions at an airport, observe conditions in a bay, etc. Further, analysis system 36 and/or remote system 42 could perform one or more actions in response to the situation, such as issue an advisory for a maximum safe speed for motor vehicles, warn when it is unsafe to land aircraft at the airport, issue a maritime fog or low visibility warning, etc.

While shown and described herein as a method and system for measuring visibility, it is understood that the invention further provides various alternative embodiments. For example, in one embodiment, the invention provides a computer-readable medium that includes computer program code to enable a computer infrastructure to measure visibility. To this extent, the computer-readable medium includes program code, such as visibility system 30 (FIG. 2), that implements each of the various process steps of the invention. It is understood that the term "computer-readable medium" comprises one or more of any type of physical embodiment of the program code. In particular, the computer-readable medium can comprise program code embodied on one or more portable storage articles of manufacture (e.g., a compact disc, a magnetic disk, a tape, etc.), on one or more data storage portions of a computing device, such as memory 22A (FIG. 2) and/or storage system 22B (FIG. 2) (e.g., a fixed disk, a read-only memory, a random access memory, a cache memory, etc.), and/or as a data signal traveling over a network (e.g., during a wired/wireless electronic distribution of the program code).

In another embodiment, the invention provides a business method that performs the process steps of the invention on a subscription, advertising, and/or fee basis. That is, a service provider could offer to measure visibility as described above. In this case, the service provider can manage (e.g., create, maintain, support, etc.) a computer infrastructure that performs the process steps of the invention for one or more customers. In return, the service provider can receive payment from the customer(s) under a subscription and/or fee agreement and/or the service provider can receive payment from the sale of advertising space to one or more third parties.

In still another embodiment, the invention provides a method of generating a system for measuring visibility. In this case, a computer infrastructure can be obtained (e.g., created, maintained, having made available to, etc.) and one or more systems for performing the process steps of the invention can be obtained (e.g., created, purchased, used, modified, etc.) and deployed to the computer infrastructure. To this extent, the deployment of each system can comprise one or more of (1) installing program code on a computing device, such as computing device 14 (FIG. 2), from a computer-readable medium; (2) adding one or more computing devices to the computer infrastructure; and (3) incorporating and/or modifying one or more existing systems of the computer infrastructure, to enable the computer infrastructure to perform the process steps of the invention.

As used herein, it is understood that the terms "program code" and "computer program code" are synonymous and mean any expression, in any language, code or notation, of a set of instructions intended to cause a computing device having an information processing capability to perform a particular function either directly or after any combination of the following: (a) conversion to another language, code or notation; (b) reproduction in a different material form; and/or (c) decompression. To this extent, program code can be embodied as one or more types of program products, such as an application/software program, component software/a library of functions, an operating system, a basic I/O system/driver for a particular computing and/or I/O device, and the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A system for measuring visibility, the system comprising:
    means for determining a lighting condition for an image;
    means for calculating a visibility based on the image; and
    means for adjusting the means for calculating based on the lighting condition, wherein the means for adjusting selects any one of: a set of visibility calculations for a daytime lighting condition, a set of visibility calculations for a nighttime lighting condition, or a set of visibility calculations comprising at least one calculation for a daytime lighting condition and at least one calculation for a nighttime lighting condition according to the lighting condition, and wherein the means for calculating calculates the visibility using the selected set of visibility calculations.

2. The system of claim 1, further comprising means for selecting a field of view for the image.

3. The system of claim 1, further comprising means for capturing the image.

4. The system of claim 3, wherein the means for capturing further includes means for filtering undesired wavelengths of light from the image.

5. The system of claim 1, wherein the image is based on light in the visible and near-infrared spectrums.

6. The system of claim 1, wherein the means for determining includes means for analyzing the image.

7. The system of claim 1, wherein the means for calculating includes:
    means for obtaining image data for a plurality of portions of the image;
    means for estimating a plurality of visual ranges using the selected set of visibility calculations, wherein each estimated visual range is based on image data for a unique one of the plurality of portions; and
    means for calculating the visibility based on the plurality of visual ranges.

8. The system of claim 7, wherein the means for estimating includes:
    means for calculating a plurality of metrics based on the image data for the unique one of the plurality of portions;
    means for estimating a plurality of metric-based visual ranges, wherein each of the plurality of metric-based visual ranges is based on a unique one of the plurality of metrics; and
    means for estimating the visual range for the one of the plurality of portions based on the plurality of metric-based visual ranges.

9. A system comprising:
    means for obtaining image data for a plurality of portions of an image; and
    means for estimating a unique visual range for each of the plurality of portions of the image, wherein each visual range is estimated based on a set of features detected in the image data for at least one of: a set of target objects or a set of light sources in a unique one of the plurality of portions.

10. The system of claim 9, further comprising means for identifying the plurality of portions in the image.

11. The system of claim 9, further comprising means for selecting the plurality of portions based on a lighting condition for the image.

12. The system of claim 9, further comprising means for calculating the visibility based on a combination of the plurality of visual ranges.

13. A system for measuring visual ranges, the system comprising:
    means for obtaining image data for a plurality of portions of an image; and
    means for estimating a plurality of visual ranges, wherein each estimated visual range is based on the image data for a unique one of the plurality of portions, and wherein the means for estimating includes:
        means for calculating a plurality of metrics based on the image data for the one of the plurality of portions;
        means for estimating a plurality of metric-based visual ranges, wherein each of the plurality of metric-based visual ranges is based on one of the plurality of metrics; and
        means for estimating the visual range for the one of the plurality of portions based on the plurality of metric-based visual ranges.

14. A system for measuring visibility, the system comprising:
    means for calculating a plurality of metrics based on an image;
    means for estimating a plurality of visual ranges, wherein each of the plurality of visual ranges is based on a unique one of the plurality of metrics; and
    means for calculating the visibility based on the plurality of visual ranges.

15. The system of claim 14, further comprising means for selecting the plurality of metrics based on a lighting condition for the image.

16. The system of claim 15, further comprising means for determining the lighting condition for the image.

17. The system of claim 14, wherein the plurality of metrics include at least one metric based on a pixel intensity for at least a portion of the image.

18. The system of claim 14, wherein the plurality of metrics include at least one metric based on a contrast between a target object in the image and a background.

19. The system of claim 14, wherein the plurality of metrics include at least one metric based on edges detected in at least a portion of the image.

20. The system of claim 14, wherein the plurality of metrics include at least one metric based on a wavelet transform of image data for at least a portion of the image.

21. The system of claim 14, wherein the plurality of metrics include at least one metric based on a number of light sources in at least a portion of the image.

22. The system of claim 14, wherein the plurality of metrics include at least one metric based on a color intensity for at least a portion of the image.

23. A system for measuring visibility, the system comprising:
- means for obtaining configuration data, wherein the configuration data is based on a set of training images, and wherein the configuration data includes a visibility curve for each unique combination of a metric and a portion of an image in the set of training images;
- means for obtaining a new image; and
- means for calculating the visibility based on the configuration data and the new image.

24. The system of claim 23, further comprising means for selecting the configuration data based on a lighting condition for the image.

25. The system of claim 23, wherein the means for calculating includes:
- means for obtaining image data for a plurality of portions of the image;
- means for estimating a plurality of visual ranges, wherein each estimated visual range is based on image data for one of the plurality of portions and at least one corresponding visibility curve for the one of the plurality of portions; and
- means for calculating the visibility based on the plurality of visual ranges.

26. The system of claim 23, wherein the means for calculating includes:
- means for calculating a plurality of metrics based on image data for at least a portion of the image;
- means for estimating a plurality of metric-based visual ranges, wherein each of the plurality of metric-based visual ranges is based on one of the plurality of metrics; and
- means for calculating the visibility based on the plurality of metric-based visual ranges.

27. The system of claim 23, further comprising means for comparing the new image to the set of training images.

28. The system of claim 23, further comprising means for adding the new image to the set of training images when the new image is sufficiently different from each training image in the set of training images.

29. The system of claim 28, further comprising means for updating the configuration data based on the new image.

30. The system of claim 23, further comprising means for periodically removing a training image from the set of training images.

* * * * *

UNITED STATES PATENT AND TRADEMARK OFFICE
CERTIFICATE OF CORRECTION

PATENT NO.       : 7,602,937 B2                                                             Page 1 of 1
APPLICATION NO.  : 11/149089
DATED            : October 13, 2009
INVENTOR(S)      : Mian et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1162 days.

Signed and Sealed this

Fifth Day of October, 2010

David J. Kappos
*Director of the United States Patent and Trademark Office*